United States Patent [19]

Ishii et al.

[11] Patent Number: 5,382,589

[45] Date of Patent: Jan. 17, 1995

[54] PHTHALIMIDE COMPOUNDS AND METHODS OF PRODUCING SAME

[75] Inventors: Akihiro Ishii, Urawa; Yasunobu Nishimura, Kawagoe; Hirotsune Kondoh, Kamifukuoka; Yoshiyuki Kikuchi, Houya, all of Japan

[73] Assignee: Central Glass Company, Limited, Ube, Japan

[21] Appl. No.: 90,136

[22] Filed: Jul. 21, 1993

[30] Foreign Application Priority Data

Jan. 30, 1991 [JP] Japan ................................. 3-010211

[51] Int. Cl.⁶ .................. A61K 31/445; C07D 401/12
[52] U.S. Cl. .......................................... 514/1; 546/193
[58] Field of Search ......................... 546/193; 514/318

[56] References Cited

U.S. PATENT DOCUMENTS

| | | | |
|---|---|---|---|
| 4,514,408 | 4/1985 | Nisato et al. | 514/212 |
| 4,710,498 | 12/1987 | Nohara et al. | 514/242 |
| 4,912,101 | 3/1990 | Hirakawa et al. | 514/210 |

OTHER PUBLICATIONS

Chemical Abstracts, JP-A-02,121,969, vol. 113: 152270c, 1990.
Chemical Abstracts, JP-A-01,175,968, vol. 112:118663c, 1990.

*Primary Examiner*—Celia Chang
*Attorney, Agent, or Firm*—Keck, Mahin & Cate

[57] ABSTRACT

The present invention relates to phthalimide compounds represented by the following general formula (I) and their acid-added salts and to methods of producing the same:

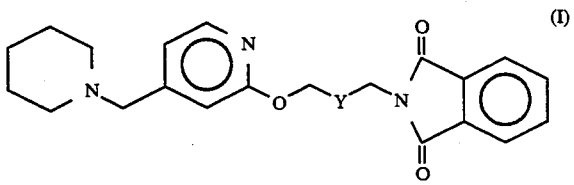

wherein Y represents $-CH_2-CH_2-$ or $-CH=CH-$. The present invention provides phthalimide compounds represented by the above general formula (I) and their acid-added salts, which are useful compounds as intermediates of medicines such as anti-ulcers based on histamine $H_2$ receptor antagonism. In particular, acid-added salts of the phthalimide compounds can be easily refined by the recrystallization method. Therefore, there is provided an advantage that purity of the anti-ulcers which are derived from phthalimide compounds and their acid-added salts according to the present invention can be improved.

8 Claims, No Drawings

PHTHALIMIDE COMPOUNDS AND METHODS OF PRODUCING SAME

TECHNOLOGICAL FIELD

The present invention relates to phthalimide compounds represented by the following general formula (I) and their acid-added salts and to methods of producing the same.

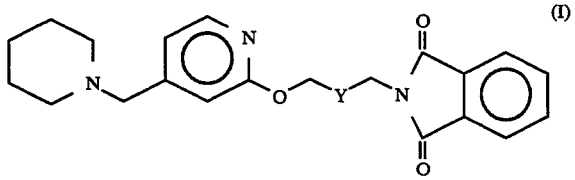

wherein Y represents —CH$_2$—CH$_2$— or —CH=CH—. Phthalimide compounds represented by the above general formula (I) and their acid-added salts are useful compounds as intermediates of medicines such as anti-ulcers based on histamine H$_2$ receptor antagonism.

BACKGROUND TECHNOLOGY

Hitherto, as an anti-peptic ulcer based on histamine H$_2$ receptor antagonism, JP-A-61-85365 has disclosed a compound represented by the following general formula (VII) and JP-A-63-225371 has disclosed a compound represented by the following general formula (VIII).

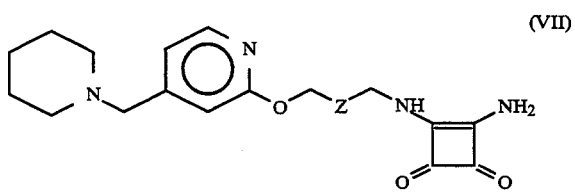

wherein Z represents —CH=CH—.

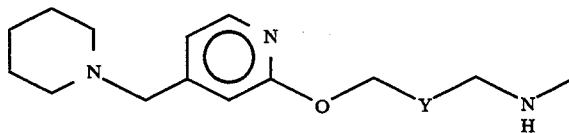

wherein Y represents —CH$_2$—CH$_2$— or —CH=CH—. As a common intermediate of these compounds, a compound which is represented by the following general formula (IX) is used.

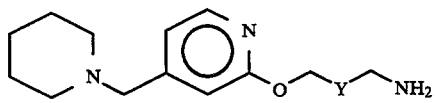

wherein Y represents —CH$_2$—CH$_2$— or —CH=CH—. As a conventional synthesis method, this compound is obtained by reacting a compound represented by the following formula (X) with a compound represented by the following formula (XI).

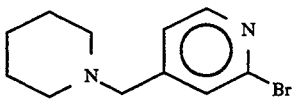

wherein Y represents —CH$_2$—CH$_2$— or —CH=CH—. However, in case that this synthesis method is used, it is industrially impossible to obtain the compounds which serve as raw materials and are represented by the above general formulas (X) and (XI), and is costly to manufacture the compounds. In the production of a compound represented by the above general formula (IX) by the reaction of a compound represented by the general formula (X) with a compound represented by the general formula (XI), there are produced many by-products and decomposed substances. Therefore, too much work is needed in refinement, and the process to produce the above intermediate (IX) is very complicated. Thus, this method has many drawbacks to be industrialized.

DISCLOSURE OF THE INVENTION

The inventors eagerly made studies in view of the problems, as a result have found that phthalimide compounds represented by the following general formula (I) and their acid-added salts are very useful for the production of the intermediate (IX), and have reached the present invention.

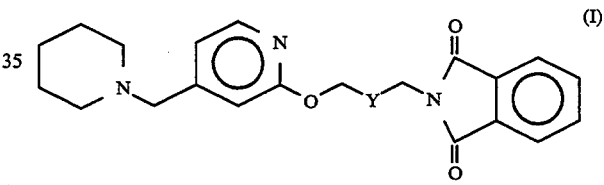

wherein Y represents —CH$_2$—CH$_2$— or —CH=CH—.

The present invention provides phthalimide com-

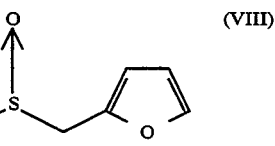

pounds represented by the following general formula (I) and their acid-added salts:

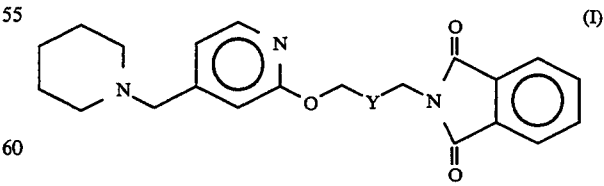

wherein Y represents —CH$_2$—CH$_2$— or —CH=CH—. The present invention further provides a method of producing phthalimide compounds represented by the following general formula (I) and their acid-added salts, which is characterized in that a pyridyloxy derivative represented by the following general formula (IV) is produced by reacting 2-chloro-4-(1-piperidinylmethyl)-pyridine represented by the following general formula (II) with an alcohol derivative represented by the following general formula (III), in that a pyridyloxy derivative represented by the following general formula (V) is produced by making a protective group "R" of a hydroxyl of the pyridyloxy derivative represented by the general formula (IV) unprotected, in that a pyridyloxy derivative represented by the following general formula (VI) is produced by halogenating or sulfonylating the pyridyloxy derivative represented by the general formula (V), in that the pyridyloxy derivative (VI) is reacted with phthalimide, and in that, if necessary, the obtained phthalimide compound is reacted with an acid, (I)

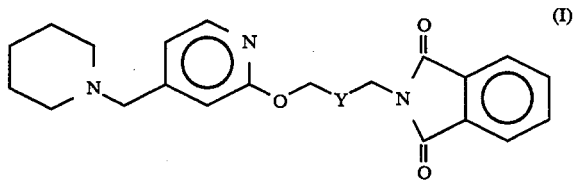

(II)

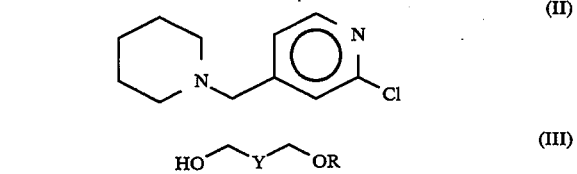

(III)

HO―Y―OR wherein, Y represents —CH$_2$—CH$_2$— or —CH=CH—, and R represents tetrahydropyranyl group, methoxymethyl group or trimethyl-silyl group of benzyl group, (IV)

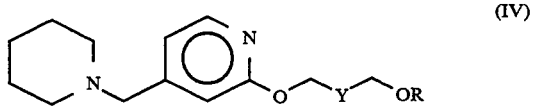

wherein Y represents —CH$_2$—CH$_2$— or —CH=CH—, and R represents tetrahydropyranyl group, methoxymethyl group or trimethyl-silyl group or benzyl group, (V)

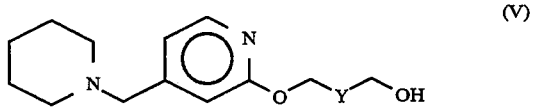

wherein Y represents —CH$_2$—CH$_2$— or —CH=CH—, (VI)

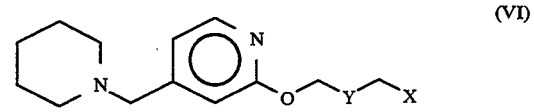

wherein Y represents —CH$_2$—CH$_2$— or —CH=CH—, and X represents Cl—, Br—, CH$_3$SO$_3$—, CF$_3$SO$_3$— or p-CH$_3$—C$_6$H$_4$—SO$_3$—. In the present invention, phthalimide compounds represented by the above general formula (I) are viscous oil-like substances having a yellow color. To be concrete, they are N-(4-(4-(1-piperidinylmethyl)pyridyl-2-oxy)-cis-2-butenyl)phthalimide, N-(4-(4-(1-piperidinylmethyl)pyridyl-2-oxy)-trans-2-butenyl)phthalimide and N(4-(4-(1-piperidinylmethyl)pyridyl-2-oxy)butyl)phthalimide.

Phthalimide compounds in the present invention, represented by the above general formula (I), can be produced, for example, in accordance with the following steps.

[First Step]

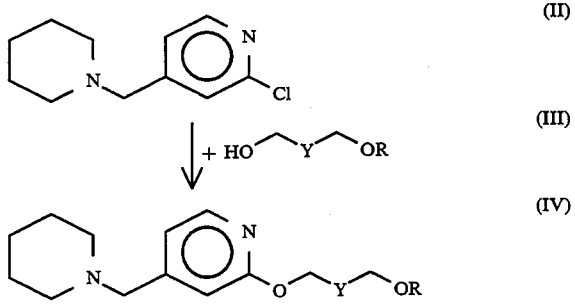

wherein Y represents —CH$_2$—CH$_2$— or —CH=CH—, and R represents tetrahydropyranyl group, methoxymethyl group or trimethyl-silyl group or benzyl group.

The present step is a step to produce pyridyloxy derivatives represented by the above general formula (IV) by reacting 2-chloro-4-(1-piperidinylmethyl)pyridine represented by the above general formula (II) with alcohol derivatives represented by the above general formula (III).

In the reaction, 2-chloro-4-(1-piperidinylmethyl)pyridine is reacted with alcohol derivatives in the molar ratio of 1 to 1. The reaction is conducted in the presence of sodium, sodium hydride, potassium, potassium hydride, lithium, lithium hydride, n-butyl lithium, sec-butyl lithium, tert-butyl lithium, tert-butoxy potassium and/or the like, and it is preferable that its amount for use is 1 to 3 equivalents relative to the substrate. It is preferable to conduct the reaction in a solvent. Examples of the solvent are tetrahydrofuran, ether, dioxane, benzene, toluene and dimethylformamide. It is preferable to have a reaction temperature ranging from 20° to 120° C.

[Second Step]

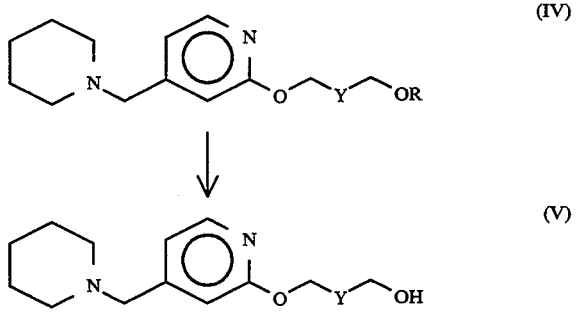

wherein Y represents —CH$_2$—CH$_2$— or —CH=CH—, and R represents tetrahydropyranyl group, methoxymethyl group or trimethyl-silyl group or benzyl group.

The present step is a step to produce pyridyloxy derivatives represented by the above general formula (V) by making the protective group "R" of a hydroxyl of pyridyloxy derivatives represented by the above general formula (IV) unprotected.

It is preferable to conduct the reaction in the presence of an acid catalyst such as hydrochloric acid, sulfuric acid, acetic acid, p-toluenesulfonic acid, p-toluenesulfonic acid pyridine salt. It is preferable that the amount of the acid catalyst is 0.1 to 3 equivalents relative to the substrate. It is preferable to conduct the reaction in a solvent. Examples of the solvent are alcohols such as methanol and ethanol, acetone-water, tetrahydrofuran-water and water. It is preferable to have a reaction temperature ranging from 0° to 80° C.

[Third Step]

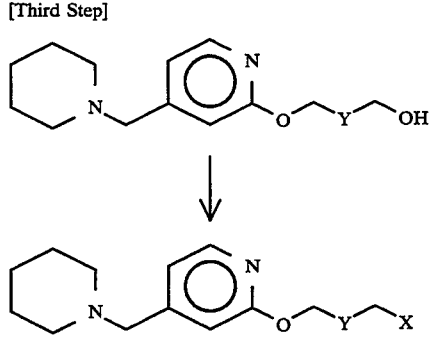

wherein Y represents —CH$_2$—CH$_2$— or —CH=CH—, and X represents Cl—, Br—, CH$_3$SO$_3$—, CF$_3$SO$_3$— or p-CH$_3$—C$_6$H$_4$—SO$_3$—.

The present invention is a step to produce pyridyloxy derivatives represented by the above general formula (VI) by halogenating or sulfonylating pyridyloxy derivatives represented by the above general formula (V).

It is preferable to conduct the reaction in the presence of thionyl chloride, tosyl chloride, methanesulfonyl chloride, trifluoromethanesulfonyl chloride, carbon tetrachloride-triphenylphosphine, carbon tetrabromide-triphenylphosphine and/or the like. It is preferable that its amount is 1 to 3 equivalents relative to the substrate. It is preferable to use base(s) such as triethylamine, pyridine, potassium carbonate and sodium carbonate in the reaction. It is preferable that its amount is 1 to 3 equivalents relative to the substrate. It is preferable to conduct the reaction in a solvent such as dichloromethane, chloroform, benzene, toluene, ethyl acetate or dimethylformamide. It is preferable to have a reaction temperature ranging from 0° to 30° C.

[Fourth Step]

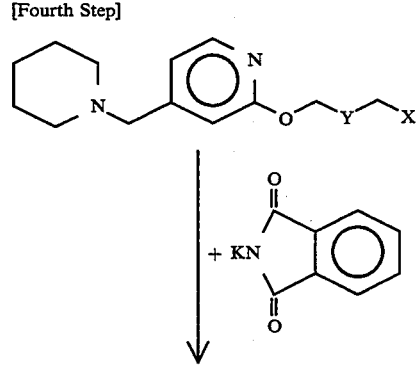

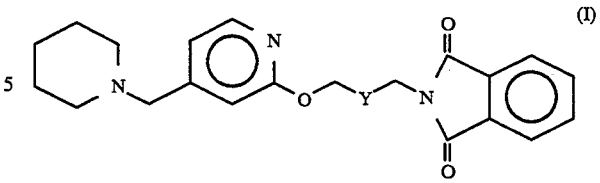

wherein Y represents —CH$_2$—CH$_2$— or —CH=CH—, and X represents Cl—, Br—, CH$_3$SO$_3$—, CF$_3$SO$_3$— or p-CH$_3$—C$_6$H$_4$—SO$_3$—.

The present step is a step to produce phthalimide compounds represented by the above general formula (I) by reacting pyridyloxy derivatives represented by the above general formula (VI) with a phthalimide.

In the reaction, the pyridyloxy derivatives are reacted with potassium phthalimide in the molar ratio of 1 to 1. If the reaction is conducted in the presence of a phase transfer catalyst, the reaction can rapidly be completed. Examples of the phase transfer catalyst are tetra-n-butylammonium hydrogensulfate, tetra-n-butylammonium chloride and tetra-n-butylammonium bromide. It is preferable that its amount is 0.01 to 3 equivalents relative to the substrate. It is preferable to conduct the reaction in a solvent such as benzene, toluene, acetonitrile or ethyl acetate. It is preferable that the reaction temperature is from 0° to 100° C.

As is mentioned hereinabove, phthalimide compounds represented by the above general formula (I) can be produced.

Phthalimide compounds represented by the above general formula (I) can be turned into acid-added salts so as no isolate them as solids in accordance with a conventional method. Examples of the acid are hydrochloric acid, hydrobromic acid, nitric acid, sulfuric acid, oxalic acid, succinic acid, maleic acid, fumaric acid, tartaric acid, lactic acid and phthalic acid. Examples of the acid-added salts of the phthalimide compounds are N-(4-(4-(1-piperidinylmethyl)pyridyl-2-oxy)-cis-2-butenyl) phthalimide.2 hydrochloric acid.ethanol salt, N-(4-(4-(1-piperidinylmethyl)pyridyl-2-oxy)-cis-2-butenyl) phthalimide.2 nitric acid salt, N-(4-(4-(1-piperidinylmethyl)pyridyl-2-oxy)-cis-2-butenyl)phthalimide.maleic acid salt, N-(4-(4-(1-piperidinylmethyl)pyridyl-2-oxy) butyl)phthalimide.fumaric acid salt. The acid-added salts of the phthalimide compounds can be refined by the recrystallization method.

The phthalimide compounds represented by the above general formula (I) and their acid-added salts can be easily turned into amines represented by the above general formula (IX) by making the phthaloyl group unprotected, and are useful compounds for the production of the above intermediate (IX). In particular, the acid-added salts of the phthalimide compounds can be easily refined by the recrystallization method. Therefore, purity of the amines represented by the above general formula (IX) can be easily improved. Thus, the acid-added salts of the phthalimide compounds are very useful compounds because purity of anti-ulcers which are derived from the amines (IX) and represented by the above general formulas (VII) and (VIII) can be also improved.

EXAMPLES

Hereinafter, the present invention is described concretely with reference to examples.

EXAMPLE 1

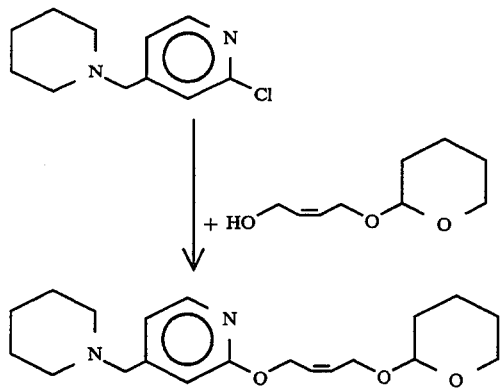

4.56 g of sodium hydride (60% purity) was suspended in 100 ml of tetrahydrofuran and 5 ml of dimethylformamide, and 15.0 g of 2-chloro-4-(1-piperidinylmethyl)-pyridine represented by the above general formula (II) and 12.3 g of 4-(2-oxytetrahydropiranyl)-cis-2-buten-1-ol represented by the above general formula (XIII) were dropped into the suspension with cooling the suspension with ice. After the dropping, the temperature was gradually raised to room temperature, and further raised to reflux the solution for 11 hr. After cooling, water was added to the reaction liquid, and the extraction was conducted by using ethyl acetate. The extract was washed with water and saturated sodium chloride solution, then dried by using anhydrous magnesium sulfate, and then filtered. After that, the solvent was distilled out, and then the refinement was conducted by silica gel column chromatography, thereby to obtain 22.5 g of 2-(4-(2-oxytetrahydropyranyl)-cis-2-buten-1-oxy)-4-(1-piperidinylmethyl)pyridine (91.3%) represented by the above general formula (XIV).

EXAMPLE 2

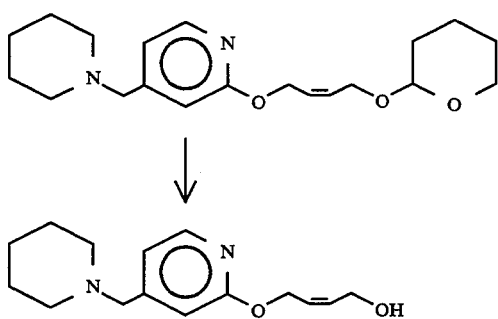

22.5 g of 2-(4-(2-oxytetrahydropyranyl)-cis-2-buten-1-oxy)-4-(1-piperidinylmethyl)pyridine represented by the above general formula (XIV) was dissolved in 100 ml of ethyl acetate. Then, 100 ml of 1N-HCl was added to the solution. After that, stirring was continued for 2 hr at room temperature. After the reaction, the aqueous layer was separated, then washed with ethyl acetate, and then turned into basic by adding thereto potassium carbonate. The aqueous layer was subjected to extraction with dichloromethane. Then, the extract was washed with saturated sodium chloride solution, then dried with anhydrous magnesium sulfate, and then filtered. The solvent was distilled out thereby to obtain 15.5 g of 4-(4-(1-piperidinylmethyl)pyridyl-2-oxy)-cis-2-buten-1-ol (91.0%) represented by the above general formula (XV).

IR (cm$^{-1}$, film) 3370, 2935, 1614

$^1$H-NMR ($\delta$, CDCl$_3$) 1.30–1.75 (6H, m), 2.23–2.52 (4H, m), 3.40 (2H, s), 3.49 (1H, bs), 4.32 (2H, d, J=6Hz), 4.99 (2H, d, J=6Hz), 5.57–6.09 (2H, m), 6.74 (1H, s), 6.89 (1H, d, J=5Hz), 8.01 (1H, d, J=5Hz)

EXAMPLE 3

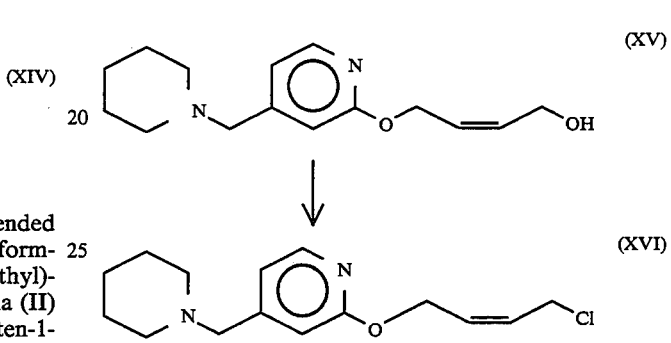

15.5 g of 4-(4-(1-piperidinylmethyl)pyridyl-2-oxy)-cis-2-buten-1-ol represented by the above general formula (XV) was dissolved in 200 ml of dichloromethane. Then, 9.4 g of anhydrous potassium carbonate was suspended in the solution, and a solution of 10.2 g of thionyl chloride in 20 ml of dichloromethane was dropped into the suspension with cooling the suspension with ice. After that, the temperature was gradually raised to room temperature, and stirring was continued for 2 hr. After the reaction, 5% sodium hydrogencarbonate solution was added to the solution. The organic layer was separated, and then was subjected to extraction with 1.5N-HCl. Then, the extract was washed with toluene, then turned into basic by potassium carbonate, and then subjected to extraction with toluene. Then, the extract was washed with saturated sodium chloride solution, then dried with anhydrous magnesium sulfate, and then filtered thereby to obtain 80 ml of toluene solution containing 14.7 g of 1-chloro-4-(4-(1-piperydinylmethyl)-pyridyl-2-oxy)-cis-2-buten (88.6%) represented by the above general formula (XVI).

EXAMPLE 4

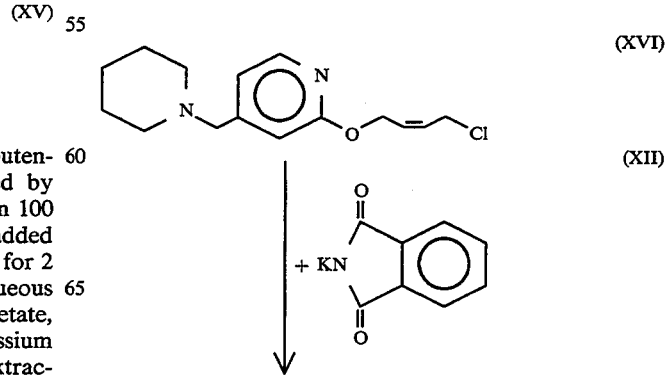

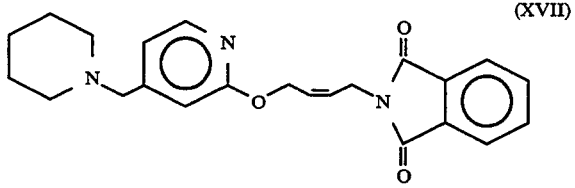

(XVII)

13.2 g of potassium phthalimide represented by the above general formula (XII) and 1.45 g of tetra-n-butylammonium hydrogensulfate were suspended in 80 ml of toluene solution containing 14.7 g of 1-chloro-4-(4-(1-piperydinylmethyl)pyridyl-2-oxy)-cis-2-buten represented by the above general formula (XVI). The reaction was continued for 2 hr at a temperature of 80° C. After cooling, the reaction liquid was washed with 1N-NaOH, then with saturated sodium chloride solution, then dried with anhydrous magnesium sulfate, and then filtered. The solvent was distilled out thereby to obtain 18.0 g of N-(4-(4-(1-piperidinylmethyl) pyridyl-2-oxy)-cis-2-butenyl)phthalimide (87.8%) represented by the above general formula (XVII).

IR (cm$^{-1}$, film) 2935, 1770, 1714, 1615

$^1$H-NMR (δ, CDCl$_3$) 1.30–1.75 (6H, m), 2.23–2.52 (4H, m), 3.41 (2H, s), 4.47 (2H, d, J=6Hz), 5.12 (2H, d, J=6Hz), 5.50–6.15 (2H, m), 6.75 (1H, s), 6.89 (2H, d, J=5Hz), 7.65–7.97 (4H, m), 8.08 (2H, d, J=5Hz)

EXAMPLE 5

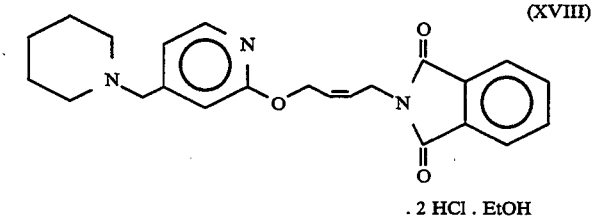

(XVIII)

. 2 HCl . EtOH 3.29 g of N-(4-(4-(1-piperidinylmethyl)pyridyl-2-oxy)-cis-2-butenyl) phthalimide represented by the above general formula (XVII) was dissolved in 30 ml of ethanol. Hydrogen chloride gas was passed through the solution with cooling the solution with ice. Precipitated white crystals were filtered, and then washed with ethanol-n-hexane, and then dried thereby to obtain 3.70 g of N-(4-(4-(1-piperidinylmethyl)pyridyl-2-oxy)-cis-2-butenyl)phthalimide.2 hydrochloric acid.ethanol salt (86.2%) represented by the above general formula (XVIII).

m.p. 155°–170° C. (decomposition)

IR (cm$^{-1}$, KBr) 3408, 2948, 2632, 2532, 1768, 1714, 1616, 1394, 1294

$^1$H-NMR (δ, DMSO-d$_6$) 1.06 (3H, t, J=7Hz), 1.29–1.42 (1H, m), 1.67–1.94 (5H, m), 2.80–2.91 (2H, m), 3.28 (2H, d, J=12Hz), 3.45 (2H, q, J=7Hz), 4.26 (2H, d, J=76Hz), 4.36 (2H, d, J=7Hz), 5.05 (2H, d, J=6Hz), 5.62–5.71 (1H, m), 5.80–5.89 (1H, m), 7.18 (1H, s), 7.32 (1H, d, J=6Hz), 7.82–7.91 (4H, m), 8.25 (! H, d, J=6Hz), 11.20 (1H, broad)

EXAMPLE 6

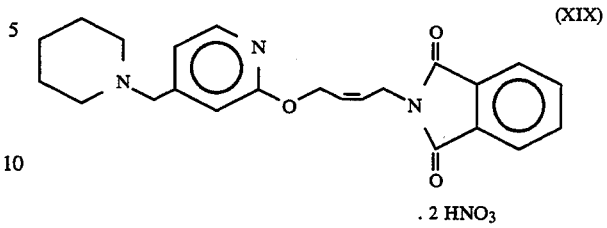

(XIX)

. 2 HNO$_3$ 2.25 g of N-(4-(4-(1-piperidinylmethyl)pyridyl-2-oxy)-cis-2-butenyl)phthalimide represented by the above general formula (XVII) was dissolved in 30 ml of ethanol, then 1.3 ml of concentrated nitric acid (61% purity) was added to the solution, and then the solution was cooled for two days in a refrigerator. Precipitated crystals were filtered, and then dried thereby to obtain 2.70 g of N-(4-(4-(1-piperidinylmethyl)pyridyl-2-oxy)-cis-2-butenyl)phthalimide.2 nitric acid salt (90.7%) represented by the above general formula (XIX).

m.p. 114°–116° C. (decomposition)

IR (cm$^{-1}$, KBr) 2944, 2636, 1770, 1714, 1642, 1394, 1280

$^1$H-NMR (δ, DMSO-d$_6$) 1.30–2.00 (6H, m), 2.65–3.20 (2H, m), 3.20–3.55 (2H, m), 4.36 (2H, s), 4.38 (2H, d, J=6Hz), 5.10 (2H, d, J=6Hz), 5.55–6.05 (2H, m), 7.06 (1H, s), 7.19 (1H, d, J=5Hz), 7.91 (4H, s), 8.32 (1H, d, J=5Hz), 9.53 (2H, bs)

EXAMPLE 7

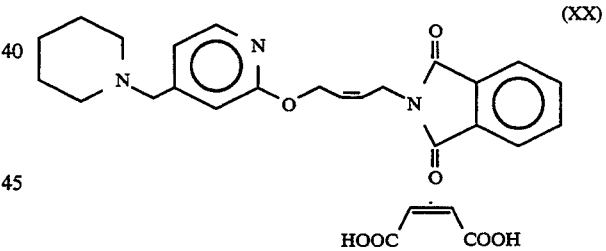

(XX)

3.33 g of N-(4-(4-(1-piperidinylmethyl)pyridyl-2-oxy)-cis-2-butenyl)phthalimide represented by the above general formula (XVII) was dissolved in 35 ml of ethanol, then 1.09 g of maleic acid was added to the solution, and then the solution was cooled with ice for two hr. Precipitated white crystals were filtered and then dried, thereby to obtain 4.00 g of N-(4-(4-(1-piperidinylmethyl)pyridyl-2-oxy)-cis-2-butenyl)phthalimide.maleic acid salt (92.6%) represented by the above general formula (XX).

m.p. 148°–150° C. (decomposition)

IR (cm$^{-1}$, KBr) 3468, 2940, 2536, 1770, 1710, 1620, 1568, 1456, 1392, 1066, 990, 874, 718

$^1$H-NMR (δ, DMSO-d$_6$) 1.36–1.93 (6H, m), 2.90–3.20 (4H, m), 4.23 (2H, s), 4.39 (2H, d, J=6Hz), 5.09 (2H, d, J=6Hz), 5.55–6.00 (2H, m), 6.12 (2H, s), 7.02 (1H, s), 7.16 (1H, d, J=5Hz), 7.92 (4H, s), 8.31 (1H, d, J=5Hz)

EXAMPLE 8

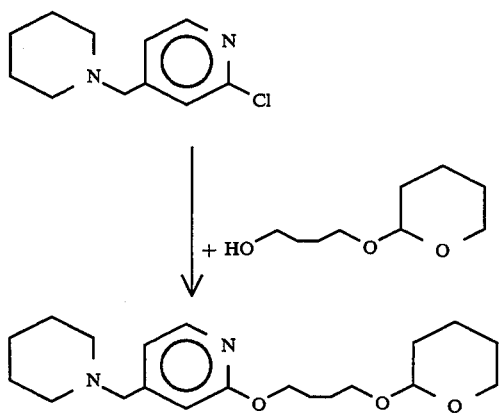

13.29 g of sodium hydride (60% purity was suspended in 250 ml of tetrahydrofuran and 15 ml of dimethylformamide, and then 50.0 g of 2-chloro-4-(1-piperidinylmethyl)pyridine represented by the above general formula (II) and 41.4 g of 4-(2-oxytetrahydropiranyl)-butane-1-ol represented by the above general formula (XXI) were dropped into the suspension with cooling the suspension with ice. After the dropping, the temperature was gradually raised to room temperature, and further raised so as to reflux the solution for 15 hr. After cooling, water was added to the reaction liquid, and the extraction was conducted by using ethyl acetate. The extract was washed with water and saturated sodium chloride solution, then dried by using anhydrous magnesium sulfate, and then filtered. After that, the solvent was distilled out, and then the refinement was conducted by silica gel column chromatography thereby to obtain 74.5 g of 2-(4-(2-oxytetrahydropyranyl)-butane-1-oxy)-4-(1-piperidinylmethyl)pyridine (90.1%) represented by the above general formula (XXII).

EXAMPLE 9

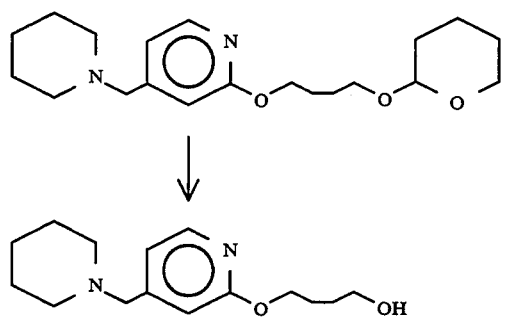

74.5 g of 2-(4-(2-oxytetrahydropyranyl)-butane-1-oxy)-4-(1-piperidinylmethyl)pyridine represented by the above general formula (XXII) was dissolved in 400 ml of ethyl acetate. Then, 340 ml of 1N-HCl was added to the solution. After that, stirring was continued for 12 hr at room temperature. After the reaction, the aqueous layer was separated, then washed with ethyl acetate, and then turned into basic by adding thereto potassium carbonate. The aqueous layer was subjected to extraction with ethyl acetate. Then, the extract was washed with saturated sodium chloride solution, then dried with anhydrous magnesium sulfate, and then filtered. The solvent was distilled out thereby to obtain 50.4 g of 4-(4-(1-piperidinylmethyl)pyridyl-2-oxy)-butane-1-ol (89.2%) represented by the above general formula (XXIII).

$^1$H-NMR (δ, CDCl$_3$) 1.00–2.04 (10H, m), 2.12–2.52 (4H, m), 2.75 (1H, broad), 3.41 (2H, s), 3.71 (2H, t, J=6Hz), 4.31 (2H, t, J=6Hz), 6.71 (1H, s), 6.85 (1H, d, J=5Hz), 8.03 (1H, d, J=5Hz)

EXAMPLE 10

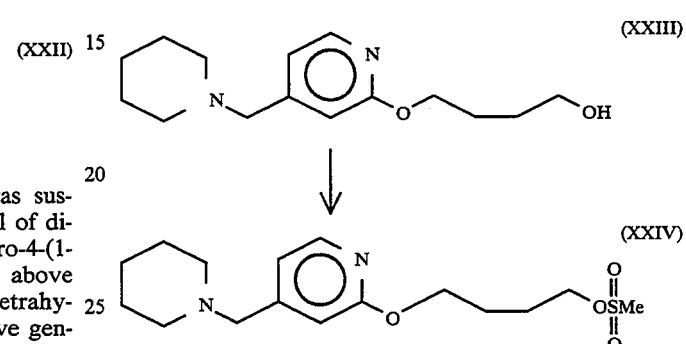

50.0 g of 4-(4-(1-piperidinylmethyl)pyridyl-2-oxy)-butane-1-ol represented by the above general formula (XXIII) was dissolved in 500 ml of dichloromethane, and then 47.8 g of triethylamine was added to the solution. Then, 36.8 g of methanesulfonyl chloride was dropped into the solution with cooling the solution with ice. After the dropping, the temperature was gradually raised to room temperature, and then stirring was continued for 1 hr. After the reaction, 5% sodium hydrogencarbonate was added to the solution, and then the organic layer was separated. The organic layer was dried with anhydrous magnesium sulfate, and then filtered. The solvent was distilled out, thereby to obtain 58.5 g of 1-methanesulfonyloxy-4-(4-(1-piperidinylmethyl) pyridyl-2-oxy)-butane (94.8%) represented by the above general formula (XXIV).

$^1$H-NMR (δ, CDCl$_3$) 1.09–1.75 (6H, m), 1.75–2.10 (4H, m), 2.16–2.53 (4H, m), 3.02 (3H, s), 3.41 (2H, s), 4.04–4.48 (4H, m), 6.71 (1H, s), 6.86 (1H, d, J=5Hz), 8.03 (1H, d, J=5Hz)

EXAMPLE 11

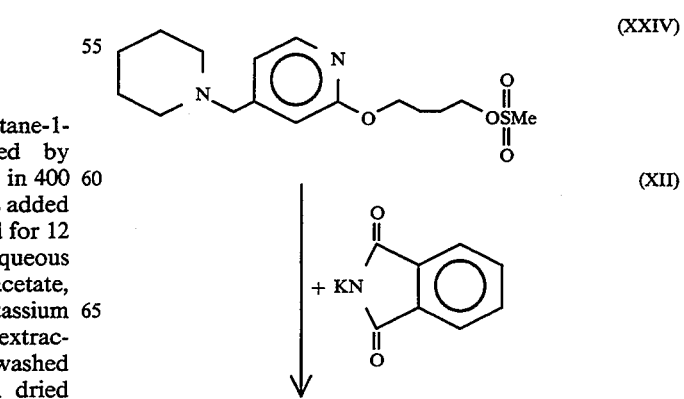

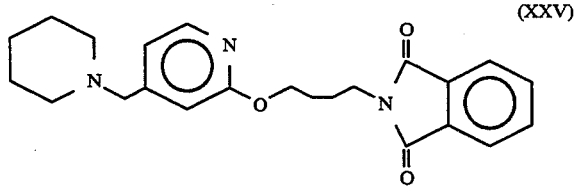

58.5 g of 1-methanesulfonyloxy-4-(4-(1-piperidinylmethyl)pyridyl-2-oxy)-butane represented by the above general formula (XXIV) was dissolved in 400 ml of acetonitrile. Then, 52.6 g of potassium phthalimide represented by the above general formula (XII and 3.9 g of tetra-n-butylammonium hydrogensulfate were suspended in the solution. The suspension was refluxed for 5 hr. After cooling, the reaction liquid was filtered, and then the solvent was distilled out. Residues were dissolved in ethyl acetate, and then the solution was washed with 1N-NaOH, then with saturated sodium chloride solution, then dried by using anhydrousmagnesium sulfate, and then filtered. The solvent was distilled out, thereby to obtain 60.2 g of N-(4-(4-(1-piperidinylmethyl)pyridyl-2-oxy)butyl phthalimide (85.4%) represented by the above general formula (XXV).

m.p. 46°–48 °C.

IR (cm$^{-1}$, film) 2940, 2856, 2796, 1772, 1712, 1614, 1560, 1470, 1422, 1398, 1372, 1044, 720

$^1$H-NMR (δ, CDCl$_3$) 1.24–1.72 (6H, m), 1.72–1.99 (4H, m), 2.20–2.48 (4H, m), 3.39 (2H, s), 3.60–3.88 (2H, In), 4.14–4.41 (2H. m), 6.67 (1H, s), 6.83 (1H, d, J=5Hz), 7.52–7.92 (4H, m), 8.02 (1H, d, J=5Hz)

EXAMPLE 12

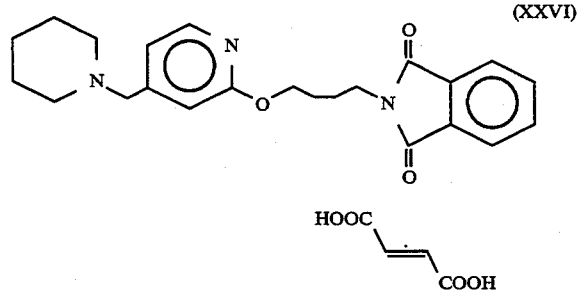

0.50 g of N-(4-(4-(1-piperidinylmethyl)pyridyl-2-oxy)butyl)phthalimide represented by the above general formula (XXV) and 0.37 g of fumaric acid were dissolved in 20 ml of ethanol with heating the solution. The amount of the solution was concentrated to about 5 ml under reduced pressure. The concentrated solution was left for 12 hr with cooling the solution with ice. Precipitated crystals were filtered, and then dried thereby to obtain 0.52 g of N-(4-(4-(1-piperidinylmethyl)pyridyl-2-oxy)butyl)phthalimide.fumaric acid salt (80.3%) which takes the form of white crystals and is represented by the above general formula (XXVI).

m.p. 104°–106° C.

IR (cm$^{-1}$, KBr) 3460, 2948, 2640, 2540, 1768, 1712, 1650, 1612, 1562, 1428, 1398, 1364, 1306, 1168, 1058, 984, 714, 646

$^1$H-NMR (δ, DMSO-d$_6$) 1.20–1.98 (10H, m), 2.32–2.68 (4H, m), 3.42–3.80 (2H, s, 2H, m), 4.08–4.40 (2H, m), 6.62 (2H, s), 6.74 (1H, s), 6.93 (1H, d, J=5Hz), 7.84 (4H, s), 8.05 (1H, d, J=5Hz), 9.22 (2H, broad)

Advantages of the Invention

The present invention provides phthalimide compounds represented by the above general formula (I) and their acid-added salts, which are useful compounds as intermediates of medicines such as anti-ulcers based on histamine H$_2$ receptor antagonism. In particular, acid-added salts of the phthalimide compounds can be easily refined by the recrystallization method. Therefore, there is provided an advantage that purity of the anti-ulcers, which are represented by the above general formulas (VII) and (VIII) and derived from phthalimide compounds and their acid-added salts according to the present invention, can improved.

We claim:

1. Phthalimide compounds which are represented by the following general formula (I) and acid-added salts of the same:

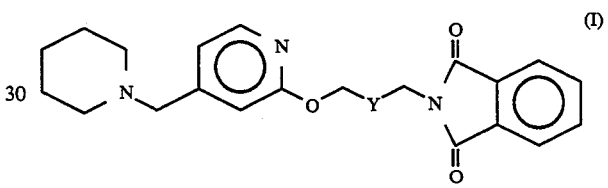

wherein Y represents —CH$_2$—CH$_2$— or —CH=CH—.

2. Compounds according to claim 1, wherein said compounds comprise N-(4-(4-(1-piperidinylmethyl)-pyridyl-2-oxy)-cis-2-butenyl) phthalimide and acid-added salts of the same.

3. Compounds according to claim 2, wherein said compounds comprise N-(4-(4-(1-piperidinylmethyl)-pyridyl-2-oxy)-cis-2-butenyl)phthalimide.2 hydrochloric acid.ethanol salt.

4. Compounds according to claim 2, wherein said compounds comprise N-(4-(4-(1-piperidinylmethyl)-pyridyl-2-oxy)-cis-2-butenyl)phthalimide.2 nitric acid salt.

5. Compounds according to claim 2, wherein said compounds comprise N-(4-(4-(1-piperidinylmethyl)-pyridyl-2-oxy)-cis-2-butenyl)phthalimide.maleic acid salt.

6. Compounds according to claim 1, wherein said compounds comprise N-(4-(4-(1-piperidinylmethyl)-pyridyl-2-oxy)-trans-2-butenyl)phthalimide and acid-added salts of the same.

7. Compounds according to claim 1, wherein said compounds comprise N-(4-(4-(1-piperidinylmethyl)-pyridyl-2-oxy)butyl)phthalimide and acid-added salts of the same.

8. Compounds according to claim 7, wherein said compounds comprise N-(4-(4-(1-piperidinylmethyl)-pyridyl-2-oxy)butyl)phthalimide.fumaric acid salt.

* * * * *